US010328016B2

(12) United States Patent
Kerl et al.

(10) Patent No.: US 10,328,016 B2
(45) Date of Patent: Jun. 25, 2019

(54) DYE COMPOSITION WITH SPECIAL NON-IONIC LINEAR SILICONE POLYMERS

(71) Applicant: Henkel AG & Co. KGaA, Duesseldorf (DE)

(72) Inventors: Sylvia Kerl, Hamburg (DE); Susanne Bietz, Elmshorn (DE); Camille Grosjacques, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/454,727

(22) Filed: Mar. 9, 2017

(65) Prior Publication Data

US 2017/0172897 A1 Jun. 22, 2017

Related U.S. Application Data

(63) Continuation of application No. PCT/EP2015/068878, filed on Aug. 18, 2015.

(30) Foreign Application Priority Data

Sep. 9, 2014 (DE) .................. 10 2014 217 994

(51) Int. Cl.
| | | |
|---|---|---|
| A61K 8/891 | (2006.01) | |
| A61K 8/39 | (2006.01) | |
| A61Q 5/06 | (2006.01) | |
| A61Q 5/10 | (2006.01) | |
| A61K 8/86 | (2006.01) | |
| A61K 8/06 | (2006.01) | |
| A61Q 5/00 | (2006.01) | |

(52) U.S. Cl.
CPC .............. *A61K 8/891* (2013.01); *A61K 8/06* (2013.01); *A61K 8/062* (2013.01); *A61K 8/39* (2013.01); *A61K 8/86* (2013.01); *A61Q 5/00* (2013.01); *A61Q 5/065* (2013.01); *A61Q 5/10* (2013.01); *A61K 2800/4322* (2013.01); *A61K 2800/4324* (2013.01); *A61K 2800/882* (2013.01)

(58) Field of Classification Search
CPC . A61K 8/891; A61K 8/86; A61K 8/06; A61K 8/39; A61K 8/062; A61K 2800/4324; A61K 2800/4322; A61K 2800/882; A61Q 5/10; A61Q 5/065

USPC ............................................................ 8/405
See application file for complete search history.

(56) References Cited

U.S. PATENT DOCUMENTS

| | | |
|---|---|---|
| 2001/0042276 A1 | 11/2001 | Kawasoe et al. |
| 2006/0123564 A1 | 6/2006 | Nishizawa et al. |
| 2009/0053159 A1 | 2/2009 | Brun |
| 2009/0119852 A1* | 5/2009 | Marsh ..................... A61K 8/34 8/408 |
| 2010/0037404 A1 | 2/2010 | Koike et al. |
| 2010/0172859 A1* | 7/2010 | Matsunaga ............ A61K 8/361 424/70.27 |
| 2011/0229425 A1 | 9/2011 | Sasao et al. |
| 2014/0165301 A1 | 6/2014 | Schweinsberg et al. |

FOREIGN PATENT DOCUMENTS

| | | |
|---|---|---|
| JP | 2005/139133 A | 6/2005 |
| JP | 2006/028119 A | 2/2006 |
| JP | 2008/285415 A | 11/2008 |

OTHER PUBLICATIONS

STIC Search Report dated May 6, 2017.*
"PCT International Search Report (PCT/EP2015/068878) dated Sep. 10, 2015".
XP055199592_Wacker Siliconöle AK_Jan. 1, 2001 (Jan. 1, 2001).
Liu X. M. et. al.; "Comparative Studies of Poly(DimethylSiloxanes) Using Automated GPC-MALDI-TOF MS and On-Line GPC-ESI-TOF MS"; Am. Soc. Mass. Spectrom., 2003, 14, 195-202.
XP002745019 Mintel Mar. 2003 3 Minutes Hair color (pure orange).
XP002745020 Mintel Aug. 2011 Step Color.
XP002745018 Beauty with Impact Dow Corning 2014.

* cited by examiner

*Primary Examiner* — Eisa B Elhilo
(74) *Attorney, Agent, or Firm* — James J. Cummings

(57) ABSTRACT

A cosmetic agent for dyeing keratin fibers, in particular human hair, includes at least one special non-ionic linear silicone polymer and at least one oxidation dye pre product and/or a direct dye. The use of the at least one non-ionic linear silicone polymer leads to an improved colorfulness and/or depth of shades. A corresponding packaging unit (kit of parts) and a method for dyeing keratin fibers both include the cosmetic agent. The cosmetic agent and packaging unit including the same are used for increasing the colorfulness and/or depth of shades.

7 Claims, No Drawings

DYE COMPOSITION WITH SPECIAL NON-IONIC LINEAR SILICONE POLYMERS

FIELD OF THE INVENTION

The present invention relates to cosmetic agents for dyeing keratinic fibers, which include special nonionic linear silicone polymers.

Furthermore, the present invention relates to a packaging unit (kit of parts), which includes a cosmetic agent of the invention and an oxidizing agent preparation.

Moreover, the present invention relates to a method for dyeing keratinic fibers with use of a cosmetic agent of the invention as well as an oxidizing agent preparation.

In addition, the present invention relates to the use of a cosmetic agent of the invention for increasing the colorfulness and/or the depth of shades.

Lastly, the present invention relates to the use of a packaging unit of the invention for producing a cosmetic agent for changing the color of keratinic fibers with an increased colorfulness and/or depth of shades.

BACKGROUND OF THE INVENTION

The changing of the shape and color of hair is an important field in modern cosmetics. As a result, the appearance of the hair can be adapted both to current fashion trends and to the individual wishes of the individual consumer. The fashionable color design of hairstyles or the covering of gray or white hair with trendy or natural color tones typically occurs with color-modifying agents. Apart from a high coloring performance, these agents should have additional properties, such as, for example, the increase in hair volume.

Various coloring systems are known in the prior art for providing color-modifying cosmetic agents, in particular, for the skin or for keratin-containing fibers such as, for example, human hair.

So-called oxidation dyes are used for permanent, intensive colors with suitable fastness properties. Such dyes customarily include oxidation dye precursors, so-called developer components and coupler components. The developer components form the actual dyes under the influence of oxidizing agents or atmospheric oxygen with one another or during coupling with one or more coupler components.

The oxidation dyeing agents are indeed characterized by excellent, long-lasting coloring results. For natural-looking colors, however, customarily a mixture of a relatively large number of oxidation dye precursors must be used; in many cases, direct dyes are used, furthermore, for providing nuances.

Coloring or tinting agents, which include so-called direct dyes as the coloring component, are customarily used for temporary colors. These are dye molecules that are directly absorbed onto the substrate and do not require any oxidative process to develop the color. These dyes include, for example, henna which was already known in antiquity for dyeing skin and hair. These dyes are as a rule markedly more sensitive to shampooing than oxidative dyes, so that an often undesirable shift in shades or even a visible homogeneous color loss occurs much earlier.

Lastly, a further dyeing method has attracted great interest. In this method, precursors of the natural hair dye melanin are applied to the substrate, e.g., hair; these then form bioanalogous dyes in the course of oxidative processes in the hair. 5,6-Dihydroxyindoline, for example, is used as the dye precursor in such a method. Particularly, in the case of repeated use of agents which include 5,6 dihydroxyindoline, it is possible to restore the natural hair color in persons with gray hair. Coloring can occur here with atmospheric oxygen as the sole oxidizing agent, so that other oxidizing agents need not be used. In persons originally having medium-blond to brown hair, 5,6-dihydroxyindoline can be used as the sole dye precursor. For use in persons having an originally red and in particular dark to black hair color, in contrast, satisfactory results can often be achieved only by the concurrent use of further dye components, in particular special oxidation dye precursors.

However, the oxidative dyeing agents, known in the prior art, do not always lead to the desired high coloring performance, in particular to a high colorfulness and/or a high color depth.

The object of the present invention, therefore, was to provide a cosmetic agent for dyeing keratinic fibers, which avoids or at least reduces the disadvantages of the prior art and which results in an improved colorfulness and/or color depth.

Furthermore, other desirable features and characteristics of the present invention will become apparent from the subsequent detailed description of the invention and the appended claims, taken in conjunction with this background of the invention.

BRIEF SUMMARY OF THE INVENTION

A first subject of the invention, therefore, is a cosmetic agent for changing the color of keratinic fibers, comprising in a cosmetically acceptable carrier
a) at least one compound, selected from the group of oxidation dye precursors, direct dyes, and mixtures thereof,
b) at least one nonionic linear silicone polymer of the formula (I)

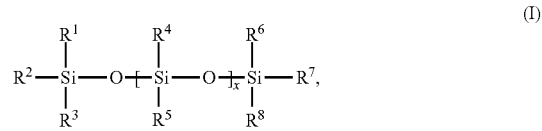

where
x stands for integers from 10 to 10,000, and
R1 to R7, in each case independently of one another, stand for hydrogen, a hydroxy group, a linear or branched C1-4 alkyl group, or a linear or branched C1-20 hydroxyalkyl group.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It was now found surprisingly that the addition of at least one special nonionic linear silicone polymer to cosmetic agents for dyeing keratinic fibers results in an improved colorfulness of shades. An indicator for the colorfulness of shades is chroma. The higher the chroma value, the higher the colorfulness of the shade. The colorfulness can be increased visually still further if the depth of color is also increased. A higher chroma value and an increased depth of color are obtained according to the invention by adding at least one special nonionic linear silicone polymer.

According to the above formulas and all following formulas, a chemical bond labeled with the symbol "*" stands for a free valence of the corresponding structural fragment. A free valence in this case is understood to be the number of atomic bonds that originate from the corresponding structural fragment at the position labeled with the symbol "*." In the context of the present invention, preferably in each case an atomic bond originates from the positions, labeled with the symbol "*," of the structural fragments to other structural fragments.

The term "keratinic fibers or keratin fibers as well" according to the invention is understood to mean pelts, wool, feathers, and human hair. It is particularly preferred in the context of the present invention if the cosmetic agents are used for dyeing human hair.

Furthermore, the term "nonionic linear silicone polymers" in the context of the present invention is understood to mean silicone polymers that are unbranched and have no permanently anionic or permanently cationic groups and no anionizable or cationizable groups, such as, for example, carboxylic acid groups or amine groups.

In addition, the term "combability" in the context of the present invention is understood to mean both the combability of wet fibers and also the combability of dry fibers.

Moreover, the term "fatty alcohols" in the context of the present invention is understood to mean aliphatic, long-chain, monohydric, primary alcohols, which have unbranched hydrocarbon groups having 6 to 30 carbon atoms. The hydrocarbon groups can be saturated but also mono- or polyunsaturated.

Lastly, the term "fatty acids" in the context of the present invention is understood to mean aliphatic monocarboxylic acids with unbranched carbon atoms, which have hydrocarbon groups having 6 to 30 carbon atoms. The hydrocarbon groups can be either saturated or also mono- or polyunsaturated.

The specification of the total amount in regard to the components of the cosmetic agent of the invention in the present case, unless specified otherwise, refers to the total amount of active substance of the particular component. Furthermore, the specification of the total amount in regard to the components of the cosmetic agent of the invention, unless specified otherwise, refers to the total weight of the oxidizing agent-free cosmetic agent of the invention.

The cosmetic agents of the invention include a cosmetic carrier. According to the invention, the cosmetic carrier is preferably aqueous, alcoholic, or aqueous-alcoholic. For example, creams, emulsions, gels, or surfactant-containing foaming solutions such as, for example, shampoos, foam aerosols, or other preparations, suitable for use on hair, are used in the context of the present invention.

An aqueous carrier in the context of the invention includes at least 30% by weight, particularly at least 50% by weight of water, based on the total weight of the cosmetic agent.

Aqueous-alcoholic carriers in the context of the present invention are to be understood to be water-containing compositions, which include a C1-C4 alcohol in a total amount of 3 to 90% by weight, based on the total weight of the cosmetic agent, in particular ethanol or isopropanol.

The cosmetic agents of the invention can include in addition further organic solvents such as, for example, methoxybutanol, ethyl diglycol, 1,2-propylene glycol, n-propanol, n-butanol, n-butylene glycol, glycerol, diethylene glycol monoethyl ether, and diethylene glycol mono-n-butyl ether. Preferred in this case are all water-soluble organic solvents, the solvent being included in a total amount of 0.1 to 30% by weight, preferably of 1 to 20% by weight, in particular of 2 to 10% by weight, based on the total weight of the cosmetic agent.

The cosmetic agent of the invention includes as a first essential component a) a compound selected from the group of oxidation dye precursors (ODP), direct dyes (DD), and mixtures thereof.

In one preferred embodiment, the cosmetic agents of the invention include at least one oxidation dye precursor.

Oxidation dye precursors based on their reaction behavior can be divided into two categories, so-called developer components and coupler components. Developer components can form the actual dye with themselves. They can therefore be present as the only compounds in the cosmetic agent of the invention. In one preferred embodiment, the cosmetic agents of the invention therefore include at least one oxidation dye precursor of the developer type. It can also be provided in the context of the present invention, however, that the cosmetic agents of the invention include at least one oxidation dye precursor of the coupler type. Especially good results are obtained in regard to the dyeing of keratinic fibers, if the cosmetic agents of the invention include at least one oxidation dye precursor of the developer type and at least one oxidation dye precursor of the coupler type.

The developer and coupler components are usually used in the free form. In the case of substances with amino groups, however, it can be preferred to use the salt form thereof, in particular in the form of the hydrochlorides and hydrobromides or sulfates.

Cosmetic agents are preferred according to the invention that include the developer and/or coupler components each in a total amount of 0.001 to 10% by weight, primarily of 0.01 to 8% by weight, preferably of 0.1 to 5% by weight, in particular of 0.5 to 3% by weight, based on the total weight of the cosmetic agent.

In another preferred embodiment, the cosmetic agent of the invention is therefore characterized in that it includes an oxidation dye precursor of the developer and/or coupler type in a total amount of 0.001 to 10% by weight, primarily of 0.01 to 8% by weight, preferably of 0.1 to 5% by weight, in particular of 0.5 to 3% by weight, based on the total weight of the cosmetic agent.

Suitable oxidation dye precursors of the developer type are, for example, p-phenylenediamine and the derivatives thereof. Preferred p-phenylenediamines are selected from one or more compounds of the group formed by p-phenylenediamine, p-toluylenediamine, 2-chloro-p-phenylenediamine, 2,3-dimethyl-p-phenylenediamine, 2,6-dimethyl-p-phenylenediamine, N,N-bis(2-hydroxyethyl)-p-phenylenediamine, 2-(2-hydroxyethyl)-p-phenylenediamine, 2-(1,2-dihydroxyethyl)-p-phenylene diamine, N-(2-hydroxypropyl)-p-phenylenediamine, N-(4'-aminophenyl)-p-phenylene diamine, 2-methoxymethyl-p-phenylenediamine, N-phenyl-p-phenylenediamine, 2-(2-hydroxyethyl)-p-phenylenediamine, and N-(4-amino-3-methylphenyl)-N-[3-(1H-imidazol-1-yl)propyl]amine, and the physiologically acceptable salts thereof.

It can be preferable, furthermore, according to the invention to use compounds that include at least two aromatic rings substituted with amino and/or hydroxyl groups as developer component. Preferred bicyclic developer components are selected from N,N'-bis(2-hydroxyethyl)-N,N'-bis(4'-aminophenyl)-1,3-diaminopropan-2-ol, N,N'-bis(4- aminophenyl)-1,4-diazacycloheptane, bis(2-hydroxy-5-aminophenyl)methane, and the physiologically acceptable salts thereof.

It can be preferred, furthermore, according to the invention to use a p-aminophenol derivative or one of the physiologically acceptable salts thereof as a developer component. Preferred p aminophenols are p-aminophenol, N-methyl-p-aminophenol, 4-amino-3-methylphenol, 4-amino-2-aminomethylphenol, 4-amino-2-(1,2-dihydroxyethyl)phenol, 4-amino-2-(diethylaminomethyl)phenol, and the physiologically acceptable salts thereof.

Further, the developer component can be selected from o-aminophenol and the derivatives thereof, preferably from 2-amino-4-methylphenol, 2-amino-5-methylphenol, 2-amino-4-chlorophenol, and/or the physiologically acceptable salts thereof.

Furthermore, the developer component can be selected from heterocyclic developer components, such as pyrimidine derivatives, pyrazole derivatives, pyrazolopyrimidine derivatives, or the physiologically acceptable salts thereof. Preferred pyrimidine derivatives are 2,4,5,6-tetra aminopyrimidine, 4-hydroxy-2,5,6-triaminopyrimidine, and the physiologically acceptable salts thereof. A preferred pyrazole derivative is 4,5-diamino-1-(2-hydroxyethyl)pyrazole and the physiologically acceptable salts thereof. Pyrazolo[1,5-a]pyrimidines are preferred in particular as pyrazolopyrimidines.

Preferred oxidation dye precursors of the developer type are selected from the group formed by p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxy methyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-amino phenyl)methane, 1,3-bis(2,5-diaminophenoxy)propan-2-ol, N,N'-bis(4-aminophenyl)-1,4-diaza cyclo heptane, 1,10-bis(2,5-diaminophenyl)-1,4,7,10-tetraoxadecane, p-aminophenol, 4-amino-3-methyl phenol, 4-amino-2-aminomethylphenol, 4-amino-2-(1,2-dihydroxyethyl)phenol and 4-amino-2-(diethyl aminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, or the physiologically acceptable salts of said compounds.

Particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole, and the physiologically acceptable salts thereof.

According to a further preferred embodiment of the present invention, the cosmetic agent of the invention includes as the oxidation dye precursor, apart from at least one developer component, furthermore in addition at least one coupler component. m-Phenylenediamine derivatives, naphthols, resorcinol and resorcinol derivatives, pyrazolones, and m-aminophenol derivatives are generally used as coupler components.

Coupler components preferred according to the invention are selected from
  a) m-aminophenol and derivatives thereof, in particular 3-aminophenol, 5-amino-2-methylphenol, 3-amino-2-chloro-6-methylphenol, 5-amino-4-chloro-2-methylphenol, 5-(2'-hydroxyethyl)amino-2-methylphenol, and 2,4-dichloro-3-aminophenol,
  b) o-aminophenol and derivatives thereof, such as 2-amino-5-ethylphenol,
  c) m-diaminobenzene and derivatives thereof such as, for example, 2,4-diamino-phenoxyethanol, 1,3-bis(2',4'-diaminophenoxy)propane, 1-methoxy-2-amino-4-(2'-hydroxyethylamino)benzene, 2,6-bis(2'-hydroxyethylamino)-1-methylbenzene, 2-({3-[(2-hydroxy ethyl)amino]-4-methoxy-5-methylphenyl}amino)ethanol, and 2-({3-[(2-hydroxy ethyl)amino]-2-methoxy-5-methylphenyl}amino)ethanol,
  d) o-diaminobenzene and derivatives thereof,
  e) di- or trihydroxybenzene derivatives, in particular resorcinol, 2-chlororesorcinol, 4-chloro-resorcinol, 2-methylresorcinol, and 1,2,4-trihydroxybenzene,
  f) pyridine derivatives, in particular 3-amino-2-methylamino-6-methoxypyridine, 2,6-diamino pyridine, 2,6-dihydroxy-3,4-dimethylpyridine, 2-amino-3-hydroxypyridine, and 3,5-diamino-2,6-dimethoxypyridine,
  g) naphthalene derivatives, such as 1-naphthol and 2-methyl-1-naphthol,
  h) morpholine derivatives, such as 6-hydroxybenzomorpholine,
  i) quinoxaline derivatives,
  j) pyrazole derivatives, such as 1-phenyl-3-methylpyrazol-5-one,
  k) indole derivatives, such as 6-hydroxyindole,
  l) pyrimidine derivatives, or
  m) methylenedioxybenzene derivatives, such as 1-(2'-hydroxyethyl)amino-3,4-methylenedioxybenzene, and the physiologically acceptable salts thereof.

Coupler components preferred according to the invention are selected from the group, formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxy ethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethyl phenyl} amino)-ethanol, 2-[3-morpholin-4-ylphenyl)amino]ethanol, 3-amino-4-(2-methoxyethoxy)-5-methylphenyl amine, 1-amino-3-bis(2-hydroxyethyl)aminobenzene, resorcinol, 2-methylresorcinol, 4-chloro resorcinol, 1,2,4-trihydroxybenzene, 2-amino-3-hydroxypyridine, 3-amino-2-methylamino-6-methoxy pyridine, 2,6-dihydroxy-3,4-dimethylpyridine, 3,5-diamino-2,6-dimethoxypyridine, 1-phenyl-3-methylpyrazol-2-one, 1-naphthol, 1,5-dihydroxynaphthalene, 2,7-dihydroxynaphthalene, 1,7-dihydroxy naphthalene, 1,8-dihydroxynaphthalene, 4-hydroxyindole, 6-hydroxyindole, 7-hydroxy indole, 4-hydroxyindoline, 6-hydroxyindoline, 7-hydroxyindoline, or the physiologically acceptable salts of the aforementioned compounds.

Coupler components particularly preferred according to the invention are resorcinol, 2 methylresorcinol, 5-amino-2-methylphenol, 3-aminophenol, 2-(2,4-diaminophenoxy)ethanol, 1,3bis(2,4-diaminophenoxy)propane, 1-methoxy-2-amino-4-(2'-hydroxyethylamino)benzene, 2 amino-3-hydroxypyridine, 2,6-dihydroxy-3,4-dimethylpyridine, 1,5-dihydroxynaphthalene, 2,7 dihydroxynaphthalene, and 1-naphthol, and the physiologically acceptable salts thereof.

In a particularly preferred embodiment of the present invention, the cosmetic agents of the invention are characterized in that they include as the oxidation dye precursor at least one developer component, selected from the group comprising p-phenylenediamine, p-toluylendiamine, N,N-bis(2-hydroxyethyl)amino-p-phenylenediamine, 1,3-bis[(2-hydroxyethyl-4'-aminophenyl)amino]propan-2-ol, 1,10-bis (2',5'-diaminophenyl)-1,4,7,10-tetraoxadecane, 4-aminophenol, 4-amino-3-methylphenol, bis(5-amino-2-hydroxyphenyl)methane, 2,4,5,6-tetraaminopyrimidine, 2-hydroxy-4,5,6-triamino ⌐ pyrimidine, 4,5-diamino-1-(2-hydroxyethyl)pyrazole, the physiologically acceptable salts thereof and mixtures thereof, and at least one coupler component, selected from the group comprising resorcinol, 2-methylresorcinol, 5-methylresorcinol, 2,5-dimethylresorcinol, 4-chlororesorcinol, resorcinol monomethyl ether, 5-aminophenol, 5-amino-2-methylphenol, 5-(2-hydroxyethyl)amino-2-methylphenol, 3-amino-4-chloro-2-methylphenol, 3-amino-2-chloro-6-methylphenol, 3-amino-2,4-dichlorphenol, 2,4-diaminophenoxyethanol, 2-amino-4-(2'-hydroxyethyl)aminoanisole sulfate, 1,3 bis(2,4-diaminophenoxy)propane, 2-amino-3-hydroxypyridine, 2-methylamino-3-amino-6-methoxypyridine, 2,6-dihydroxy-3,4-dimethylpyridine, 3,5-diamino-2,6-dimethoxypyridine, 1 naphthol, 2-methyl-1-naphthol, 1,5-dihydroxynaphthalene, 2,7-dihydroxynaphthalene, 1-phenyl-3-methylpyrazol-5-one, 2,6-bis[(2'-hydroxyethyl)amino] toluene, 4-hydroxyindole, 6-hydroxyindole, 6 hydroxybenzomorpholine, and the physiologically acceptable salts thereof and mixtures thereof.

To obtain a balanced and subtle shade formation, it can also be provided in the context of the present invention that the cosmetic agents of the invention in addition include at least one direct dye. Direct dyes are dyes that are directly absorbed onto the hair and do not require any oxidative process to develop the color. Direct dyes are usually nitrophenylenediamines, nitroaminophenols, azo dyes, anthraquinones, or indophenols.

Direct dyes can be divided into anionic, cationic, and nonionic direct dyes.

Preferred anionic direct dyes are the compounds known under the names: Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, and tetrabromophenol blue. Preferred cationic direct dyes are cationic triphenylmethane dyes, such as Basic Blue 7, Basic Blue 26, Basic Violet 2, and Basic Violet 14, and aromatic systems, which are substituted with a quaternary nitrogen group, such as Basic Yellow 57, Basic Red 76, Basic Blue 99, Basic Brown 16, and Basic Brown 17 and HC Blue 16, as well as Basic Yellow 87, Basic Orange 31, and Basic Red 51. Preferred nonionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis(2-hydroxyethyl)amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1 amino-4-(2-hydroxyethyl)amino-5-chloro-2-nitrobenzene, 4-amino-3-nitrophenol, 1-(2'-ureido ⌐ ethyl) ⌐ amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Furthermore, naturally occurring dyes as well can be used as direct dyes, as are found, for example, in henna red, henna neutral, henna black, chamomile blossoms, sandalwood, black tea, walnut, buckthorn bark, sage, logwood, madder root, catechu, and alkanna root.

Preferably the cosmetic agent of the invention includes the direct dyes in a total amount of 0.001 to 10% by weight, primarily of 0.01 to 8% by weight, preferably of 0.1 to 5% by weight, in particular of 0.5 to 3% by weight, based on the total weight of the cosmetic agent.

The cosmetic agents of the invention include at least one special nonionic linear silicone polymer as the second essential component b). The addition of this special silicone polymer leads to an improved colorfulness and/or depth of shades, so that a rather small amount of dyes or dye precursors, such as developer components, coupler components, direct dyes and mixtures thereof, must be used to obtain an identical colorfulness as when cosmetic agents without special nonionic linear silicone polymers are used.

According to a preferred embodiment of the present invention, in the structural unit of the formula (I) the R1 to R7 groups, in each case independently of one another, stand for a linear C1-4 alkyl group, in particular for a methyl group.

Especially good results in the context of the present invention are obtained, if in the structural unit of the formula (I) the R1 to R7 groups, in each case independently of one another, stand for a linear C1-4 alkyl group, in particular for a methyl group, and x stands for integers from 1500 to 10,000, primarily from 1550 to 9500, preferably from 1600 to 9000, in particular from 1650 to 8500.

It is preferred in the context of this embodiment, if the nonionic linear silicone polymer of the formula (I) has an average molecular weight Mw of 111,100 to 740,000 Da, primarily of 114,000 to 703,000 Da, preferably of 118,000 to 665,000 Da, in particular of 122,000 to 628,000 Da. The average molecular weight Mw can be determined, for example, by gel permeation chromatography (GPC) (Liu X. M. et al.; "Comparative studies of poly(dimethylsiloxanes) using automated GPC MALDI-TOF MS and on-line GPC-ESI-TOF MS"; J. Am. Soc. Mass. Spectrom., 2003, 14, pages 195 to 202).

Furthermore, especially good results are obtained, if in the structural unit of the formula (I) the R1 to R7 groups, in each case independently of one another, stand for a linear C1-4 alkyl group, in particular for a methyl group, and x stands for integers from 1500 to 10,000, primarily from 1550 to 9500, preferably from 1600 to 9000, in particular from 1650 to 8500.

It is preferred according to the invention in the context of this embodiment if the nonionic linear silicone polymer of the formula (I) has an average molecular weight Mw of 111,100 to 740,000 Da, primarily of 114,000 to 703,000 Da, preferably of 118,000 to 665,000 Da, in particular of 122, 000 to 628,000 Da. The average molecular weight Mw of the special nonionic silicone polymers can be determined preferably by the aforementioned GPC method.

Particularly preferably according to the invention, the cosmetic agent includes at least two linear nonionic silicone polymers different from one another,
a) the first linear nonionic silicone polymer (SP1) having the formula (II),

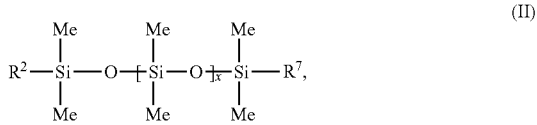

(II)

where
R2 and R7, in each case independently of one another, stand for a methyl group or a hydroxyl group, and
x stands for integers from 1500 to 10,000, primarily from 1550 to 9500, preferably from 1600 to 9000, in particular from 1650 to 8500, and b) the second linear nonionic silicone polymer (SP2) having the formula (III),

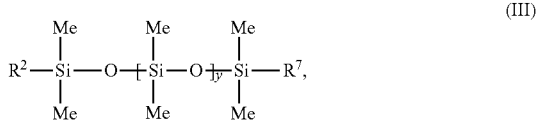

(III)

where
R2 and R7, in each case independently of one another, stand for a methyl group or a hydroxyl group, and
y stands for integers from 10 to 1499, primarily from 20 to 1400, preferably from 30 to 1350, in particular from 40 to 1300.

The use of this mixture comprising two special nonionic linear silicone polymers (SP1) and (SP2) with different average molecular weights Mw results in an improved colorfulness and/or depth of shades. As a result, the amount of employed dye in comparison with cosmetic agents, which include no special nonionic linear silicone polymers, can be reduced considerably without negatively influencing the colorfulness of the corresponding shades, however.

In the context of this embodiment, it is preferable according to the invention, if the nonionic linear silicone polymer (SP1) of the formula (II) has an average molecular weight Mw of 111,100 to 740,000 Da, primarily of 114,000 to 703,000 Da, preferably of 118,000 to 665,000 Da, in particular of 122,000 to 628,000 Da, and the nonionic linear silicone polymer (SP2) of the formula (III) has an average molecular weight Mw of 750 to 110,000 Da, primarily of 1500 to 103,000 Da, preferably of 2200 to 100,000 Da, in particular of 3000 to 97,000 Da. When the mixture of nonionic linear silicone polymers (SP1) and (SP2) with the aforementioned different average molecular weights Mw is used, especially good results are obtained in regard to increased colorfulness and/or depth of shades.

Preferably, the at least one nonionic linear silicone polymer b) is present in the form of an emulsion, wherein the emulsion has particles with an average particle diameter D50 of 0.01 μm to 10,000 μm, primarily of 0.01 μm to 100 μm, in particular of 0.3 μm to 30 μm. Special nonionic linear silicone polymers, which are present as an emulsion with the aforementioned particle size, result in an especially high colorfulness and/or depth of shades. The average particle diameter D50 can be determined, for example, by dynamic light scattering (DLS).

The cosmetic agents of the invention include the at least one nonionic linear silicone polymer b) in a total amount of 0.0005 to 15% by weight, primarily of 0.001 to 10% by weight, preferably of 0.005 to 5.0% by weight, more preferably of 0.01 to 3.0% by weight, in particular of 0.05 to 1.0% by weight, based on the total weight of the cosmetic agent. The use of the aforementioned total amount of the at least one special nonionic linear silicone polymer leads to an improved colorfulness and/or depth of shades. Furthermore, the aforementioned amounts of the special nonionic linear silicone polymer make sure that no incompatibilities occur with other ingredients of the cosmetic agent of the invention, so that when these amounts are used, a high storage stability of the cosmetic agents is assured.

It has emerged that an addition of polyoxyethylene (23) lauryl ether can stabilize the at least one nonionic linear silicone polymer, in particular the nonionic linear silicone polymer of the formulas (II) and (III), in the cosmetic agents of the invention, so that the colorfulness and/or depth of shades can be enhanced further. Cosmetic agents preferred according to the invention therefore include in addition polyoxyethylene (23) lauryl ether in a total amount of 1×10-5 to 1.5% by weight, primarily of 3×10-5 to 0.8% by weight, preferably of 1×10-4 to 0.4% by weight, more preferably of 3×10 4 to 0.2% by weight, in particular of 1×10-3 to 0.05% by weight, based on the total weight of the cosmetic agent, based on the total weight of the cosmetic agent.

The at least one nonionic linear silicone polymer, in particular the nonionic silicone polymer of the formulas (II) and (III), can be stabilized further by the addition of an ethoxylated primary alcohol. It is therefore preferable in the context of the present invention, if the cosmetic agents of the invention include in addition an ethoxylated primary alcohol in a total amount of 5×10-6 to 1.0% by weight, primarily of 1×10-5 to 0.4% by weight, preferably of 5×10-5 to 0.3% by weight, more preferably of 1×10 4 to 0.2% by weight, in particular of 5×10-4 to 0.01% by weight, based on the total weight of the cosmetic agent, the ethoxylated primary alcohol having the formula (IV)

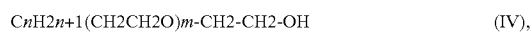

$C_nH_{2n+1}(CH2CH2O)_m\text{-}CH2\text{-}CH2\text{-}OH$     (IV), where n stands for integers from 8 to 20, primarily from 10 to 18, in particular from 12 to 15, and m stands for integers from 1 to 8, primarily from 1 to 6, preferably from 2 to 5, in particular for 2 or 3. Suitable as an ethoxylated primary alcohol in the context of the present invention, for example, is the compound known under the INCI name C12-15 Pareth-3.

The cosmetic agents of the invention can include additional active substances and additives. It is therefore preferred in the context of the present invention, if the cosmetic agent in addition includes at least one further compound, selected from the group comprising (i) thickeners; (ii) linear or branched, saturated or unsaturated alcohols having 8 to 20 carbon atoms; (iii) surfactants, in particular amphoteric surfactants; (iv) alkalizing agents; (v) oils; as well as (vi) mixtures thereof.

Preferably, the cosmetic agents of the invention are formulated as flowable preparations. In this case, the cosmetic agents should be formulated so that, on the one hand, they can be applied and distributed well at the application site but, on the other, are sufficiently viscous, so that they remain at the site of action during the contact time and do not run.

It has proven advantageous according to the invention, therefore, if the cosmetic agents of the invention include at least one thickener from the group comprising (i) anionic, synthetic polymers; (ii) cationic, synthetic polymers; (iii) naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions and derivatives such as amylose, amylopectin, and dextrins, as well as cellulose derivatives such as, for example, methylcellulose, carboxyalkyl celluloses, and hydroxyalkyl celluloses; (iv) nonionic, synthetic polymers, such as polyvinyl alcohol or polyvinylpyrrolidinone; (v) inorganic thickeners, in particular phyllosilicates such as, for example, bentonite, particularly smectites, such as montmorillonite or hectorite; as well as (vi) mixtures thereof, in a total amount of 0.0005 to 5.0% by weight, primarily of 0.001 to 3.0% by weight, preferably of 0.005 to 1.0% by weight, in particular of 0.008 to 0.01% by weight, based on the total weight of the cosmetic agent.

It has emerged as advantageous in the context of the present invention, if at least one naturally occurring thickener, in particular xanthan gum and salts thereof, is included as a thickener in a total amount of 0.0005 to 5.0% by weight, primarily of 0.001 to 1.0% by weight, preferably of 0.005 to 0.5% by weight, in particular of 0.01 to 0.1% by weight, based on the total weight of the cosmetic agent.

It can be preferred in the context of the present invention, if the linear or branched, saturated or unsaturated alcohol having 8 to 20 carbon atoms is selected from the group comprising myristyl alcohol (1-tetradecanol), stearyl alcohol (1-octadecanol), cetearyl alcohol, 2-octyldodecanol, arachyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), primarily 2-octyldodecanol and/or cetearyl alcohol, and is included in a total amount of 1.0 to 35% by weight, primarily of 5.0 to 30% by weight, preferably of 10 to 25% by weight, in particular of 12 to 20% by weight, based on the total weight of the cosmetic agent.

Preferably the cosmetic agents of the invention can include, furthermore, at least one partial ester from a polyol having 2 to 6 carbon atoms and linear saturated carboxylic acids having 12 to 30, in particular 14 to 22 carbon atoms, wherein the partial ester can be hydroxylated, in a total amount of 0.5 to 10% by weight, in particular of 3.0 to 8.0% by weight, based on the total weight of the cosmetic agent. Such partial esters are in particular the mono- and diesters of glycerol or the monoesters of propylene glycol or the mono- and diesters of ethylene glycol or the mono-, di-, tri-, and tetraesters of pentaerythritol in each case with linear saturated C12-C30 carboxylic acids, which may be hydroxylated, in particular those with palmitic and stearic acid, the sorbitan mono-, di-, or triesters of linear saturated C12-C30 carboxylic acids, which may be hydroxylated, in particular those of myristic acid, palmitic acid, stearic acid, or of mixtures of these fatty acids and the methyl glucose mono- and diesters of linear saturated C12-C30 carboxylic acids, which may be hydroxylated.

In the context of the present invention, it can be provided that the cosmetic agents of the invention include at least one polyol partial ester, selected from glycerol monostearate, glycerol monopalmitate, glycerol distearate, glycerol dipalmitate, ethylene glycol monostearate, ethylene glycol monopalmitate, ethylene glycol distearate, ethylene glycol dipalmitate, and mixtures thereof, in particular mixtures of glycerol monostearate, glycerol monopalmitate, glycerol distearate, and glycerol dipalmitate in a total amount of 0.5 to 10% by weight, in particular of 3.0 to 8.0% by weight, based on the total weight of the cosmetic agent.

The use of the aforementioned alcohols, partial esters, and poly partial esters in the cosmetic agents of the invention can be particularly preferred when the cosmetic agents of the invention are present in the form of an oil-in-water emulsion.

It can be provided according to the invention, furthermore, that the cosmetic agents according to the invention include at least one surfactant. Surfactants in the context of the present invention are amphiphilic (bifunctional) compounds, which consist of at least one hydrophobic and at least one hydrophilic moiety. A basic property of surfactants and emulsifiers is the oriented absorption on interfaces and the aggregation to form micelles and the formation of lyotrophic phases.

According to one preferred embodiment of the present invention, the cosmetic agents of the invention include at least one amphoteric surfactant in a total amount of 0.1 to 5.0% by weight, in particular of 0.2 to 2.0% by weight, based on the total weight of the cosmetic agent. Surface-active compounds that have at least one quaternary ammonium group and at least one —COO(-) or —SO3( ) group can be called amphoteric or zwitterionic surfactants.

The compounds listed below are particularly preferred as amphoteric surfactants in the context of the present invention:

alkyl betaines having 8 to 20 carbon atoms in the alkyl group,
amidopropyl betaines having 8 to 20 carbon atoms in the acyl group,
sulfobetaines having 8 to 20 carbon atoms in the acyl group, and
amphoacetates or amphodiacetates having 8 to 20 carbon atoms in the acyl group.

In a particularly preferred embodiment, the cosmetic agents of the invention include as a surfactant at least one amphoteric surfactant, selected from amidopropyl betaines having 9 to 13 carbon atoms in the acyl group, in a total amount of 0.1 to 5.0% by weight, in particular of 0.2 to 2.0% by weight, based on the total weight of the cosmetic agent.

It can be provided, furthermore, that the cosmetic agents of the invention include at least one ethoxylated nonionic surfactant in a total amount of 0.5 to 6.0% by weight, in particular of 1.0 to 4.0% by weight, based on the total weight of the cosmetic agent. The ethoxylated nonionic surfactants in this case are different from the aforementioned ethoxylated primary alcohols. In this case, it has emerged as especially advantageous, if the ethoxylated nonionic surfactant has an HLB value above 10, preferably above 13. It is necessary to this end that the nonionic surfactant has a sufficiently high ethoxylation degree. In this regard, the cosmetic agent of the invention therefore includes as the ethoxylated nonionic surfactant at least one ethoxylated surfactant with at least 12 ethylene oxide units. Apart from the suitably ethoxylated fatty alcohols, in particular lauryl alcohol, myristyl alcohol, cetyl alcohol, stearyl alcohol, arachyl alcohol, and behenyl alcohol, in particular the adducts of 20 to 60 mol of ethylene oxide to castor oil and hydrogenated castor oil are especially suitable according to the invention. The at least one ethoxylated nonionic surfactant is preferably selected from surfactants with the INCI name Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil, and mixtures of these substances, selected particularly preferably from Ceteth-20, Steareth-20, Ceteareth-20, Ceteth-30, Steareth-30, and Ceteareth-30.

Cosmetic agents in the context of the present invention normally have a basic pH, in particular between pH 8.0 and pH 12. These pH values are necessary to assure an opening of the outer cuticle layer (cuticle) and to enable penetration of the oxidation dye precursors and/or the oxidizing agent into the hair.

The aforementioned pH can be established preferably with the use of an alkalizing agent. In the context of the present invention, the alkalizing agent is selected from the group of (i) inorganic alkalizing agents; (ii) organic alkalizing agents; and (iii) mixtures thereof, and in a total amount of 1.5 to 9.5% by weight, primarily of 2.5 to 8.5% by weight, preferably of 3.0 to 8.0% by weight, in particular of 3.5 to 7.5% by weight, based on the total weight of the cosmetic agent.

Preferred inorganic alkalizing agents are selected from the group formed by ammonia or ammonium hydroxide, therefore aqueous solutions of ammonia, sodium hydroxide, potassium hydroxide, calcium hydroxide, barium hydroxide, sodium phosphate, potassium phosphate, sodium silicate, potassium silicate, sodium carbonate, and potassium carbonate, and mixtures thereof. Ammonia or ammonium hydroxide is a particularly preferred alkalizing agent. Ammonia is particularly preferred in a total amount of 0.1 to 20% by weight, preferably of 0.5 to 10% by weight, in particular of 1.0 to 7.0% by weight, based on the total weight of the cosmetic agent.

Preferred organic alkalizing agents are selected from at least one alkanolamine. Alkanolamines preferred according to the invention are selected from alkanolamines from primary, secondary, or tertiary amines with a C2-C6 alkyl parent structure, bearing at least one hydroxyl group. Particularly preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1 amino ⊓ pentan-4-ol, 2-amino-2-methylpropanol, 2-amino-2-methylbutanol, 3-amino-2-methylpropan-1-ol, 1-amino-2-methylpropan-2-ol, 3-aminopropane-1,2-diol, 2-amino-2-methyl ⊓ propane-1,3-diol, 2-amino-2-ethyl-1,3-propanediol, N,N-dimethylethanolamine, triethanolamine, diethanolamine, and triisopropanolamine. Alkanolamines very particularly preferred according to the invention are selected from the group comprising 2-aminoethan-1-ol (monoethanolamine), 2-amino-2-methylpropan-1-ol, 2-amino-2-methylpropane-1,3-diol, and triethanolamine. Particularly preferred cosmetic agents of the invention include a mixture of monoethanolamine and 2-amino-2-methylpropan-1-ol. Preferably the at least one alkanolamine is included in a total amount of 0.05 to 15% by weight, preferably of 0.5 to 10% by weight, and in particular of 3.5 to 7.5% by weight, based on the total weight of the cosmetic agent.

Other organic alkalizing agents preferred according to the invention are selected from basic amino acids, particularly preferably selected from the group formed by L-arginine, D-arginine, D/L arginine, L-lysine, D-lysine, D/L-lysine, and mixtures thereof. Basic amino acids particularly preferred according to the invention are selected from L-arginine, D-arginine, and D/L-arginine. Preferred cosmetic agents of the invention include at least one alkalizing agent, different from alkanolamines and ammonia, in a total amount of 0.05 to 5.0% by weight, in particular of 0.5 to 3.0% by weight, based on the total weight of the cosmetic agent.

In a particularly preferred embodiment, the cosmetic agents of the invention include as alkalizing agents a mixture of at least two alkanolamines different from one another, in particular of monoethanolamine and 2-amino-2-methyl-propan-1-ol, in a total amount of 0.05 to 15% by weight, preferably of 0.5 to 10% by weight, in particular of 3.5 to 7.5% by weight, based on the total weight of the cosmetic agent.

Preferably, the pH of the cosmetic agents of the invention, measured at 22° C., is 8 to 13, primarily 9.5 to 12, preferably 10 to 11.5, in particular 10.5 to 11.

In the context of the present invention, it can be preferred, furthermore, if the cosmetic agents of the invention include at least one oil, selected from the group comprising sunflower oil, corn oil, soy oil, pumpkin seed oil, grape seed oil, sesame oil, hazelnut oil, apricot kernel oil, macadamia nut oil, arara oil, castor oil, avocado oil, and mixtures thereof, in a total amount of 0.1 to 10% by weight, preferably of 0.2 to 5.0% by weight, in particular of 0.5 to 2.0% by weight, based on the total weight of the cosmetic agent. The care effect of the nonionic linear silicone polymers can be increased further by the use of at least one aforementioned oil.

Particularly preferably, the cosmetic agents of the invention include grape seed oil in a total amount of 0.1 to 10% by weight, preferably of 0.2 to 5.0% by weight, in particular of 0.5 to 2.0% by weight, based on the total weight of the cosmetic agent.

According to a particularly preferred embodiment of the present invention, the cosmetic agents of the invention present as an oil-in-water emulsion include, based on the total weight of the cosmetic agents, cetearyl alcohol in a total amount of 2.0 to 20% by weight, in particular of 5.0 to 12% by weight, and mixtures of glycerol monostereate, glycerol monopalmitate, glycerol distearate, and glycerol dipalmitate in a total amount of 0.5 to 10% by weight, preferably 3.0 to 8.0% by weight, and at least one amphoteric surfactant, selected from amidopropyl betaines having 9 to 13 carbon atoms in the acyl group, in a total amount of 0.1 to 5.0% by weight, in particular of 0.2 to 2.0% by weight, and a mixture of at least two alkanolamines different from one another, in particular of monoethanolamine and 2-amino-2-methylpropan-1-ol, in a total amount of 0.05 to 15% by weight, preferably of 0.5 to 10% by weight, and in particular of 3.5 to 7.5% by weight, and grape seed oil in a total amount of 0.1 to 10% by weight, preferably of 0.2 to 5.0% by weight, in particular of 0.5 to 2.0% by weight.

Oxidative dye compositions can also be prepared immediately before use from two or more separately packaged compositions. This lends itself in particular for separating incompatible ingredients in order to prevent a premature reaction. Separation into multi-component systems is preferred particularly when incompatibilities of the ingredients are a possibility or a risk. The oxidative dye composition in these cases is prepared by the consumer immediately before use by mixing the components. In the context of the present invention, this procedure is particularly preferred in the case of oxidative dyes, in which the cosmetic agent of the invention is present initially separated from an oxidizing agent preparation which includes at least one oxidizing agent.

A further subject of the present invention, therefore, is a packaging unit (kit of parts), comprising, packaged separately from one another, a) at least one container (C1), containing a cosmetic agent of the invention, and b) at least one container (C2), containing an oxidizing agent preparation, which includes at least one oxidizing agent and at least one acid in a cosmetically acceptable carrier.

The dyes, which can be prepared from the packaging unit of the invention and include at least one special nonionic linear silicone polymer, lead to an improved colorfulness and/or color depth of the keratinic fibers dyed with said dyeing agents. To achieve the same colorfulness as when conventional oxidative dyeing agents without special nonionic linear silicone polymers are used, the amount of dyes can be reduced considerably in the oxidative dyeing agents prepared from the packaging unit of the invention.

The term "container" in the context of the present invention is understood to mean an enclosure, which is present in the form of an optionally reclosable bottle, tube, box, a small packet, sachet, or similar enclosures. No limits are imposed on the wrapping material according to the invention. Preferably, however, these are enclosures made of glass or plastic.

The oxidizing agents in the context of the present invention are different from atmospheric oxygen. Hydrogen peroxide and the solid adducts thereof to organic and inorganic compounds can be used as oxidizing agents. Solid adducts suitable according to the invention are in particular the adducts to urea, melamine, polyvinylpyrrolidinone, and sodium borate. Hydrogen peroxide and/or one of its solid adducts to organic or inorganic compounds are particularly preferred as oxidizing agents. Preferably according to the invention, the oxidizing agent is therefore selected from the group of persulfates, chlorites, hydrogen peroxide, and adducts of hydrogen peroxide to urea, melamine, and sodium borate, in particular hydrogen peroxide.

A particularly preferred embodiment of the present invention is therefore characterized in that hydrogen peroxide is included as the oxidizing agent in a total amount of 0.5 to 15% by weight, primarily of 0.75 to 10% by weight, preferably of 1 to 7.5% by weight, particularly preferably of 1.25 to 7% by weight, in particular of 1.5 to 6.0% by weight, based on the total weight of the oxidizing agent preparation. The calculation of the total amount in this case refers to 100% $H_2O_2$.

The oxidizing agent preparations, furthermore, can include water in a total amount of 40 to 98% by weight, in particular of 65 to 85% by weight, based on the total weight of the oxidizing agent preparation.

According to a preferred embodiment of the present invention, the oxidizing agent preparations include further at least one linear saturated alkanol having 12 to 30 carbon atoms, in particular having 16 to 22 carbon atoms, in a total amount of 0.1 to 10% by weight, primarily of 0.5 to 5.0% by weight, in particular of 1.0 to 4.0% by weight, based on the total weight of the oxidizing agent preparation. Preferred in particular are cetyl alcohol, stearyl alcohol, arachidyl alcohol, behenyl alcohol, and lanolin alcohol or mixtures of said alcohols, as they are obtainable in the large-scale hydrogenation of plant and animal fatty acids, and mixtures of said alkanols. The cetearyl alcohol mixture is particularly preferred.

In a further preferred embodiment of the present invention, the oxidizing agent preparations include at least one ethoxylated nonionic surfactant, which is selected preferably from surfactants with the INCI name: Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil and mixtures of said substances, selected particularly preferably from Ceteth-20, Steareth-20, Ceteareth-20, Ceteth-30, Steareth-30, and Ceteareth-30, in a total amount of 0.1 to 10% by weight, preferably of 0.5 to 5.0% by weight, in particular of 1 to 4.0% by weight, based on the total weight of the oxidizing agent preparation.

In the context of the present invention, it can also be provided in addition that the oxidizing agent preparations include at least one ester from a carboxylic acid having 10 to 20 carbon atoms and a linear or branched alcohol having 1 to 5 carbon atoms, in particular isopropyl myristate, in a total amount of 3.0 to 25% by weight, primarily of 5.0 to 20% by weight, in particular of 8.0 to 15% by weight, based on the total weight of the oxidizing agent preparation.

According to a particularly preferred embodiment of the present invention, the oxidizing agent preparations include, based on the total weight of the oxidizing agent preparations, at least one linear saturated alkanol having 12 to 30 carbon atoms in a total amount of 0.1 to 10% by weight, preferably of 0.5 to 5.0% by weight, in particular of 1.0 to 4.0% by weight, and at least one ethoxylated nonionic surfactant, which is selected preferably from surfactants with the INCI name: Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil and mixtures of said substances, selected particularly preferably from Ceteth-20, Steareth-20, Ceteareth-20, Ceteth-30, Steareth-30, and Ceteareth 30, in a total amount of 0.1 to 10% by weight, preferably of 0.5 to 5.0% by weight, in particular of 1.0 to 4.0% by weight, and at least one ester from a carboxylic acid having 10 to 20 carbon atoms and a linear or branched alcohol having 1 to 5 carbon atoms, preferably isopropyl myristate, in a total amount of 3.0 to 25% by weight, preferably of 5.0 to 20% by weight, in particular of 8.0 to 15% by weight.

The oxidizing agent preparations of the invention include, furthermore, at least one acid. Preferred acids are selected from dipicolinic acid, edible acids such as, for example, citric acid, acetic acid, malic acid, lactic acid, and tartaric acid, dilute mineral acids such as hydrochloric acid, phosphoric acid, pyrophosphoric acid, and sulfuric acid, and mixtures thereof. The oxidizing agent preparations preferably have a pH in the range of 2 to 5, in particular of 3 to 4.

To prepare oxidative dye compositions from the packaging unit of the invention (kit of parts), the cosmetic agent of the invention in container C1 is mixed with the oxidizing agent preparation in container C2 or vice versa.

Furthermore, it can be especially advantageous according to the invention, if the packaging unit includes at least one further hair treatment agent, in particular a conditioning agent preparation, in an additional container. Said conditioning agent preparation advantageously includes at least one conditioning agent, selected from the group of cationic polymers, silicone derivatives, and oils. Moreover, the packaging unit can comprise application aids, such as combs, brushes, dye brushes, or small brushes, personal protective clothing, in particular disposable gloves, and optionally instructions for use. A dye brush is understood to be a broad brush which has a point at the handle end, which permits and simplifies the separation of fiber bundles or strands from the total amount of fibers.

The statements made about the cosmetic agents of the invention apply mutatis mutandis to the cosmetic agent of the invention in container C1 and the oxidizing agent preparation in container C2.

A further subject of the present invention is a method for dyeing keratinic fibers, wherein the method comprises the following process step:

a) providing a cosmetic agent of the invention (M1),
b) providing an oxidizing agent preparation (M2), which includes in a cosmetically acceptable carrier at least one oxidizing agent and at least one acid,
c) mixing the cosmetic agent (M1) with the oxidizing agent preparation (M2),
d) applying the mixture obtained in step c) to the keratinic fibers and leaving said mixture on the keratinic fibers for a time period of 10 to 60 minutes, preferably of 20 to 45 minutes, at room temperature and/or at least 30° C.,
e) rinsing the keratinic fibers with water and/or a cleansing composition for 1 to 5 minutes, and
f) optionally applying an aftertreatment agent to the keratinic fibers and rinsing it off after a time period of 1 to 10 minutes.

The method of the invention for dyeing keratinic fibers with the use of at least one special nonionic linear silicone polymer results in an improved colorfulness and/or depth of shades compared with the method in which no special nonionic linear silicone polymers are used. By this means, the same colorfulness can be achieved with a smaller amount of dyes as with the prior art method in which no silicone polymers of this type are used.

Room temperature in the context of the present invention is understood to be the ambient temperature that prevails without the action of external heat and is preferably from 10 to 39° C. The effect of the coloring and/or lightening preparation can be intensified by an external heat supply, for example, by means of a heating hood. The preferred contact time of the coloring and/or lightening preparation on the keratinic fiber is 10 to 60 minutes, preferably 20 to 45 minutes. After the contact time ends, the remaining dyeing agent is washed out of the keratinic fibers with the aid of a cleansing preparation, which preferably includes at least one cationic and/or anionic and/or nonionic surfactant, and/or water. Optionally, the process is repeated with a further agent. After the washing out, the keratinic fibers are optionally rinsed with an aftertreatment agent, for example, a conditioning agent, and dried with a towel or a hot air dryer. The application of the dye preparation usually occurs by hand by the user. Preferably, in this case, personal protective clothing is worn, in particular suitable protective gloves, for example, made of plastic or latex for a one-time use (disposable gloves), and optionally an apron. It is also possible, however, to apply the dyeing agents to the keratinic fibers with an application aid.

The statements made about the cosmetic agents of the invention and the packaging unit of the invention apply mutatis mutandis to cosmetic agent M1 of the invention, oxidizing agent preparation M2 of the invention, and further preferred embodiments of the method.

Moreover, a further subject of the present invention is the use of a cosmetic agent of the invention for increasing the colorfulness and/or depth of shades. The use of at least one special nonionic linear silicone polymer results in an increased colorfulness and/or depth of shades. By this means, the amount of dyes in the cosmetic agents of the invention can be reduced compared with the prior art agents without silicone polymers of this type, to achieve an identical colorfulness and/or color depth as with oxidative dyeing agents of the prior art.

The statements made about the cosmetic agents of the invention and the packaging unit of the invention apply mutatis mutandis to other preferred embodiments of the use of the invention.

Lastly, a further subject of the present invention is the use of a packaging unit of the invention for producing a cosmetic agent for changing the color of keratinic fibers with an increased colorfulness and/or depth of shades. As already stated above, the use of the invention of at least one special nonionic linear silicone polymer results in an increased colorfulness and/or depth of shades, which allows a reduction of the amount of dyes.

The statements made about the cosmetic agents of the invention and the packaging unit of the invention apply mutatis mutandis to other preferred embodiments of the use of the invention.

The following examples are intended to explain the preferred embodiments of the invention, however, without restricting them.

EXAMPLES

1. Formulations

Compositions of the employed cosmetic agents (oil-in-water emulsions, all amounts given in % by weight). The nonionic linear silicone polymer used in the following formulations is preferably a mixture comprising a silicone polymer (SP1) of the formula (II) with x=1650 to 8000, R2 and R7=methyl and an average molecular weight Mw of 122,000 to 628,000 Da and a nonionic linear silicone polymer (SP2) of the formula (III) with y=40 to 1300, R2 and R7=methyl and an average molecular weight Mw of 3000 to 97,000 Da.

| Raw material | V1 | E1* | E2* |
|---|---|---|---|
| Xanthan gum | 0.05 | 0.05 | 0.05 |
| 2-Octyldodecanol | 2.3 | 2.3 | 2.3 |
| Lanette N [a)] | 14 | 14 | 14 |
| Cetearyl alcohol | 3.9 | 3.9 | 3.9 |
| Glycerol monostearate | 6.0 | 6.0 | 6.0 |
| Glycerol 99.5% | 2.0 | 2.0 | 2.0 |
| Cocamidopropyl betaine, 40% | 2.0 | 2.0 | 2.0 |
| Monoethanolamine | 4.5 | 4.5 | 4.5 |
| 2-Amino-2-methylpropanol | 0.1 | 0.1 | 0.1 |
| Sodium sulfite, anhydrous | 0.2 | 0.2 | 0.2 |
| Caramel syrup, 75% | 0.1 | 0.1 | 0.1 |
| Grape seed oil | 1.0 | 1.0 | 1.0 |
| p-Toluylenediamine sulfate | 0.03 | 0.03 | 0.03 |
| 4-Amino-3-methylphenol | 0.3 | 0.3 | 0.3 |
| 1,3-Benzenediol | 0.04 | 0.04 | 0.04 |
| 1-Naphthol | 0.09 | 0.09 | 0.09 |
| 5-Amino-2-methylphenol | 0.2 | 0.2 | 0.2 |
| 2-Amino-6-chloro-4-nitrophenol | 0.2 | 0.2 | 0.2 |
| Nonionic linear silicone polymer ** | — | 0.60 | 1.2 |
| Water, demineralized | To 100.00 | To 100.00 | To 100.00 |

*according to the invention
** active substance
[a)] INCI name: Cetearyl alcohol, Sodium cetearyl sulfate (BASF)

The fat base was melted together at 80° C. and dispersed with a portion of the water amount. The remaining formulation components were then incorporated in sequence while stirring. The mixture was then made up with water to 100% by weight and the formulation was stirred until cold. Formulation V1 is a comparison formulation, not according to the invention, without the nonionic silicone polymer. The formulations E1 and E2 are examples of the invention.

| Oxidizing agent preparation O1 (all amounts given in % by weight) | |
|---|---|
| Raw material | O1 |
| Disodium pyrophosphate | 0.10 |
| Dipicolinic acid | 0.10 |
| Potassium hydroxide 50% | 0.22 |
| 1-Hydroxyethane-1,1-diphosphonic acid 60% | 0.25 |
| Emulgade F [b] | 4.0 |
| Cetearyl alcohol | 0.5 |
| Ceteareth-20 | 0.5 |
| Beeswax | 0.3 |
| Isopropyl myristate | 10 |
| Hydrogen peroxide 50% | 11 |
| Water, demineralized | To 100 |

[b] INCI name: Cetearyl alcohol, PEG-40 Castor oil, Sodium cetearyl sulfate (BASF)

2. Increased Colorfulness and Color Depth by the Addition of a Mixture of Nonionic Linear Silicone Polymers with Different Average Molecular Weights Mw The oxidative dyeing agents prepared in this way were each applied in a defined amount (4 g of the oxidative dyeing agent per 1 g of yak hair) to yak hair strands (12 strands each per oxidative dyeing agent) and remained on the hair strands for a contact time of 30 minutes at 32° C. Next, the remaining agents were each rinsed out of the hair strands for 2 minutes with lukewarm water; the strands were first dried with a towel and then blown dry.

All strands were measured with a colorimeter from the company Datacolor, Spectraflash 450 type. The dC and dL values used for evaluating the colorfulness and color depth result from the L*a*b color values measured for each strand as follows:

$$dC=[(ai-a0)2+(bi-b0)2]^{1/2} \text{ or } dL=Li-L0$$

a0, b0, and L0 in this case are the averages of the color values, determined from 12 measurements, of the yak hair strands treated with the oxidative dyeing agent V1, whereas ai, bi, and Li each represent the averages of the color values after the oxidative dyeing of hair strands with the oxidative dyeing agents E1 and E2.

An indicator for the colorfulness of the colors is chroma. The higher the dC value, the higher the colorfulness of the shade. The colorfulness can be increased visually still further, if the depth of color is also increased and the dL value therefore becomes lower. The dC values and the dL values for the colors during use of the cosmetic agents V1, E1, and E2 are shown in the following table. The colors with cosmetic agents E1 and E2 of the invention, which include a mixture of special nonionic linear silicone polymers in a total amount of 0.6% by weight or 1.2% by weight, in comparison with the color without the special nonionic linear silicone polymers (V1) have an improved colorfulness and color depth.

| Oxidative dyeing agents | dC | dL |
|---|---|---|
| E1 + O1 (1:1) | 1.41 | -3.27 |
| E2 + O1 (1:1) | 0.89 | -3.50 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A cosmetic agent for changing the color of keratinic fibers, comprising in a cosmetically acceptable carrier:
   at least one compound, selected from the group of oxidation dye precursors, direct dyes, and mixtures thereof;
   a first linear nonionic silicone polymer (SP1) has the formula (II),

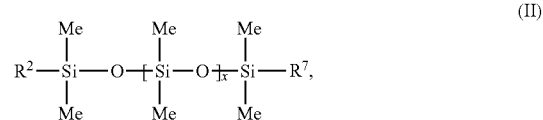

wherein
$R^2$ and $R^7$, in each case independently of one another, stand for a methyl group or a hydroxyl group, and
x stands for integers from 1,650 to 8,500; and
a second linear nonionic silicone polymer (SP2) has the formula

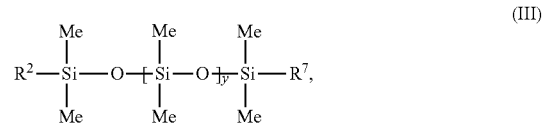

wherein
$R^2$ and $R^7$, in each case independently of one another, stand for a methyl group or a hydroxyl group, and
y stands for integers from 40 to 1300,
wherein the first and second linear nonionic silicone polymers have no carboxylic acid groups or amine groups, are included in the form of an emulsion, wherein the emulsion has particles with an average particle diameter D50 of 0.01 μm to 100 μm, and
wherein in the claimed formulae (II) and/or (III), $R^2$ and $R^7$ do not both stand for a methyl group.

2. The cosmetic agent according to claim 1, wherein the nonionic linear silicone polymer (SP1) of the formula (II) has an average molecular weight $M_w$ of 122,000 to 628,000 Da, and the nonionic linear silicone polymer (SP2) of the formula (III) has an average molecular weight $M_w$ of 3,000 to 97,000 Da.

3. The cosmetic agent according to claim 1, wherein the cosmetic agent comprises the first and second linear nonionic silicone polymers in a total amount of 0.0005 to 15% by weight based on the total weight of the cosmetic agent.

4. The cosmetic agent according to claim 1, wherein the cosmetic agent further includes polyoxyethylene (23) lauryl ether in a total amount of $1\times10^{-5}$ to 1.5% by weight based on the total weight of the cosmetic agent.

5. The cosmetic agent according to claim 1, wherein the cosmetic agent further includes an ethoxylated primary alcohol in a total amount of $5 \times 10^{-6}$ to 1.0% by weight based on the total weight of the cosmetic agent, the ethoxylated primary alcohol having the formula (IV)

$$C_nH_{2n+1}(CH_2CH_2O)_m-CH_2-CH_2-OH \quad (IV),$$

wherein n stands for integers from 8 to 20, and m stands for integers from 1 to 8.

6. A packaging unit, also known as a kit of parts, comprising, packaged separately from one another,
   a) at least one container (C1), containing a cosmetic agent according to claim 1, and
   b) at least one container (C2), containing an oxidizing agent preparation, which includes at least one oxidizing agent and at least one acid in a cosmetically acceptable carrier.

7. A method for dyeing keratinic fibers, the method comprising:
   a) providing a cosmetic agent (M1) according to claim 1,
   b) providing an oxidizing agent preparation (M2), which includes in a cosmetically acceptable carrier at least one oxidizing agent and at least one acid,
   c) mixing the cosmetic agent (M1) with the oxidizing agent preparation (M2),
   d) applying the mixture obtained in step c) to the keratinic fibers and leaving said mixture on the keratinic fibers for a time period of 10 to 60 minutes at room temperature and/or at least 30° C.,
   e) rinsing the keratinic fibers with water and/or a cleansing composition for 1 to 5 minutes, and
   f) optionally applying an aftertreatment agent to the keratinic fibers and rinsing it off after a time period of 1 to 10 minutes.

* * * * *